United States Patent [19]

Lech

[11] Patent Number: 5,402,597
[45] Date of Patent: Apr. 4, 1995

[54] METHOD AND SUBSTANCE FOR REPELLING RODENTS

[76] Inventor: Wlodek J. Lech, 53-14 72nd St., Maspeth, N.Y. 11378

[21] Appl. No.: 99,839

[22] Filed: Jul. 30, 1993

[51] Int. Cl.⁶ ............................................ A01M 13/00
[52] U.S. Cl. ................................... 43/124; 424/195.1; 43/132.1
[58] Field of Search ...................... 43/124, 131, 132.1; 424/195.1

[56] References Cited

U.S. PATENT DOCUMENTS

| | | | |
|---|---|---|---|
| 93,209 | 8/1869 | Llado | 424/195.1 |
| 244,932 | 7/1881 | Renz | 43/124 |
| 811,074 | 1/1906 | Manix | 43/132.1 |
| 1,653,710 | 12/1927 | Kitchin | 424/195.1 |
| 2,590,536 | 3/1952 | Heal | 43/124 |
| 3,002,885 | 10/1961 | Schwarcz | 43/131 |
| 4,269,820 | 5/1981 | Davies et al. | 424/10 |
| 4,671,960 | 6/1987 | Thielen | 424/195.1 |
| 5,061,491 | 10/1991 | Deryabin | 424/195.1 |

FOREIGN PATENT DOCUMENTS

| | | | |
|---|---|---|---|
| 2067846 | 7/1971 | France. | |
| 47-19440 | 3/1972 | Japan | 43/124 |
| 0348003 | 9/1960 | Switzerland. | |
| 0278816 | 10/1927 | United Kingdom | 43/124 |

OTHER PUBLICATIONS

East/West vol. 19 #5. pp. 20, 22, 24–27. "Getting the Bugs Out," May 1989. Caron Virnig.

*Primary Examiner*—P. Austin Bradley
*Assistant Examiner*—James Miner
*Attorney, Agent, or Firm*—Theodore F. Shiells

[57] ABSTRACT

A novel method for repelling rodents such as rats and mice is provided, including the step of placing an effective amount of camomile in an area where rodents are not desired.

9 Claims, No Drawings

METHOD AND SUBSTANCE FOR REPELLING RODENTS

FIELD OF THE INVENTION

The present invention relates to pest control and, in particular, to repellents for rats, mice and other rodents.

BACKGROUND OF THE INVENTION

Infestation of rodents, particularly rats and mice, in places people live and work has been a persistent problem for mankind. To eliminate rats and mice, traps of various kinds are frequently used. However, traps can be hazardous to small children and pets. Furthermore, traps are distasteful to many persons and because they require regular checking and removal of killed rodents.

Poisons of various kinds are also frequently used to eliminate rodents. The rodents ingest the poisons and are killed. Poisons, however, are undesirable because they pose a safety hazard to humans, especially children, and small pets. Poisons also are environmentally undesirable since they may ultimately enter ground water or streams. Over time, rodents may also become immune to certain poisons.

In any event, use of poisons does not eliminate the distasteful task of removal of the dead rodents. Furthermore, where poisons are used in enclosed interior spaces such as buildings, the rodents will frequently go into inaccessible areas behind walls after they ingest the poison. After the rodents die, a putrid odor may exist and become so severe as to require demolition of the wall to remove the dead rodent.

In any event, many persons find it distasteful to kill rodents and would prefer to simply repel rodents from an area. To this end, ultrasonic electronic devices have been tried. However, these devices have limited effectiveness, require a nearby electrical outlet, and may irritate house pets.

OBJECTS OF THE INVENTION

Accordingly, it is an object of the present invention to an effective rodent repellant which will not kill rodents, but will be sufficiently undesirable to rodents to cause them to leave an area where they are not desired.

It is another object of the present invention to provide a method for repelling rodents which is not hazardous to humans or common household pets.

It is another object of the present invention to provide a rodent repellant which will be effective for several months with a single application.

It is another object of the present invention to provide a repellent for rodents which is a natural substance.

It is a still further object of the present invention to provide a repellant for rodents that will be resistant to development of an immunity in rodents.

SUMMARY OF THE INVENTION

These objects, and others, are accomplished in accordance with a preferred embodiment of the present invention, which provides a method for repelling rodents comprising the step of placing an effective amount of camomile in an area where rodents are not desired.

These objects are also accomplished in accordance with another preferred embodiment of the present invention, which provides a rodent repellant consisting predominantly of camomile.

DETAILED DESCRIPTION OF THE PREFERRED EMBODIMENTS

Camomile is a common herb. It is used for a variety of medicinal purposes. Camomile is not hazardous to humans or pets. Indeed, herbal tea is sometimes made from camomile. Camomile also has a pleasant scent to humans.

Although camomile is a pleasant and edible substance to humans, it has been discovered that rodents, in particular, rats and mice, apparently find the scent of camomile extremely distasteful. When a sufficient amount of camomile is placed in an area where rats or rodents are present, either by spreading, sprinkling, placing in piles or leaving in an open container, rodents will immediately leave the area and not return. Accordingly, placing camomile in an area where rodents are not desired will effectively repel the rodents from that area. The camomile (in concentrations useful in the present invention) is non-toxic to humans, including children, and small pets. The camomile only repels the rodents but does not kill them. Thus, it is not necessary to kill the rodents to eliminate them from an area. Thus, the distasteful task of removing dead trapped or poisoned rodents from the area is avoided.

The form of camomile used in the present invention for repelling rodents is not critical. The camomile is conveniently dried and whole, in the form in which it is commonly commercially sold. The camomile may also be ground. The leaves, stems and/or flowers of the camomile plant may be used. The camomile may also be used live, that is, intentionally grown in an area where rodents are not desired. However, it has been found that the form of camomile sold as herbal tea is not fully effective and is not preferred.

In addition, since it is believed that it is the scent of camomile that is effective in repelling the rodents, the camomile may also be placed in the area to be protected in the form of a concentrated extract. Camomile extract may be made from the natural plant in an variety of well known ways, such as by boiling or solvent extraction and distillation, which need not be discussed herein. The camomile extract may also be synthesized.

The manner of placing the camomile in the area where rodents are not desired is not critical. The camomile may be sprinkled on a surface such as a floor. The camomile may also be placed in small piles in one or a plurality of locations in the area to be protected. If it is not desired to place the camomile directly on the surface, the camomile may be placed in open containers. The camomile rodent repellant of the present invention is most effective in enclosed interior areas, such as buildings.

The amount of camomile used is not critical. It is only necessary that a sufficient amount be used. In tests of the repellant of the present invention in a restaurant having approximately 4000 square feet, an amount of approximately one pint of dried and ground camomile was found to be effective. In a large, two story garage having the capacity for approximately 200 automobiles, an amount of approximately ¼ of a pound was found to be effective. However, significantly lesser or greater amounts may be used. Where there are known entrance or exit holes, it is preferable to place the camomile near those entrance and exit holes.

It is not necessary that the camomile be pure. The camomile, and may be combined with other herbs or other substances. However, the camomile is the active ingredient in the repellant of the present invention, and should not be unnecessarily diluted. Accordingly, preferably, the repellant of the present invention consists of predominantly camomile.

Because the camomile repels the rodents, but does not kill them, in applying the camomile where there is already an infestation of rodents, it is preferable to leave the rodents a "means of escape" from the area to be protected to encourage their departure. This is particularly the case in large areas, or in multi-story buildings. Thus, in applying the camomile in a large area or multi-story building, it is preferable to start at one end of the large area (or at the top floor of the multi-story building), and then to work gradually from that end (or top floor of the building) toward the other end (or lower floors) over a period of a few days or weeks to "drive" the rodents out. However, intentionally providing such a means of escape is not important in relatively small areas, since rodents will readily find a way out.

The camomile rodent repellent of the present invention will be effective for several months, and after that period of time will gradually lose potency. Accordingly, after a few months, to maintain effectiveness of the repellant, the application should be repeated.

The invention is useful in homes, restaurants, subways, train stations, garages, hospitals, schools, supermarkets, ships, and any other area where rodents are not desired. The present invention is most effective in enclosed spaces, but may also be used in the open.

Although the invention has been described in accordance with preferred embodiments, it will be seen by those skilled in the art that many modifications can be made within the sphere and scope of the present invention, and there is no intention to limit the scope of the present invention to solely these embodiments. Rather, the scope of the present invention is to be measured by the appended claims.

What is claimed is:

1. A method for repelling rodents, comprising the step of placing an effective amount of camomile in an area where rodents are not desired.

2. The method of claim 1, wherein said camomile is dried.

3. The method of claim 2, wherein said camomile is ground.

4. The method of claim 2, wherein said camomile is whole.

5. The method of claim 1, wherein said camomile is in the form of a concentrated extract.

6. The method of claim 1, wherein said step of placing includes spreading said camomile on a surface, such as a floor, in said area.

7. The method of claim 1, wherein said step of placing includes placing said Camomile in piles in a plurality of locations in said area.

8. The method of claim 1, wherein said step of placing comprises leaving said camomile in said area in an open container or containers.

9. The method of claim 1, wherein said area is an enclosed, interior area.

* * * * *